(12) United States Patent
Aimi et al.

(10) Patent No.: US 8,579,992 B2
(45) Date of Patent: Nov. 12, 2013

(54) HAIR DYE

(71) Applicant: FUJIFILM Corporation, Tokyo (JP)

(72) Inventors: Makiko Aimi, Ashigarakami-gun (JP); Minako Kasagi, Ashigarakami-gun (JP)

(73) Assignee: FUJIFILM Corporation, Tokyo (JP)

( * ) Notice: Subject to any disclaimer, the term of this patent is extended or adjusted under 35 U.S.C. 154(b) by 0 days.

(21) Appl. No.: 13/870,641

(22) Filed: Apr. 25, 2013

(65) Prior Publication Data

US 2013/0232701 A1    Sep. 12, 2013

Related U.S. Application Data

(63) Continuation of application No. PCT/JP2011/074382, filed on Oct. 24, 2011.

(30) Foreign Application Priority Data

Oct. 26, 2010 (JP) ................... 2010-239268

(51) Int. Cl.
*A61Q 5/10* (2006.01)
(52) U.S. Cl.
USPC ............. 8/405; 8/552; 8/562; 8/595; 8/611; 8/616; 8/623
(58) Field of Classification Search
USPC ............. 8/405, 552, 562, 595, 611, 616, 623
See application file for complete search history.

(56) References Cited

FOREIGN PATENT DOCUMENTS

| JP | 53-052633 A | 5/1978 |
|----|----|----|
| JP | 62-33113 A | 2/1987 |
| JP | 03-072414 A | 3/1991 |
| JP | 4-164017 A | 6/1992 |
| JP | 8-214936 A | 8/1996 |
| JP | 2001-172143 A | 6/2001 |
| JP | 2001-270812 A | 10/2001 |
| JP | 2002-37720 A | 2/2002 |
| JP | 2003-48818 A | 2/2003 |
| JP | 2003-246716 A | 9/2003 |
| JP | 2006-348011 A | 12/2006 |
| JP | 2008-273869 A | 11/2008 |
| JP | 2008273869 | * 11/2008 |

OTHER PUBLICATIONS

English abstract of the Japanese Patent No. JP 2008-273869 dated Nov. 2008.*
English translation of the International Preliminary Report on Patentability mailed May 10, 2013 for International Application No. PCT/JP2011/074382.
International Preliminary Report on Patentability mailed May 10, 2013 for International Application No. PCT/JP2011/074382.
International Search Report for PCT/JP2011/074382 dated Jan. 24, 2012.

* cited by examiner

*Primary Examiner* — Eisa Elhilo
(74) *Attorney, Agent, or Firm* — Sughrue Mion, PLLC

(57) ABSTRACT

It is an object of the present invention to provide a safe hair dye, which has a good dyeing property and is easy-to-use, and which has less uneven dyeing and has high stability of the formulation. The present invention provides a hair dye which comprises a combination of (1) a first gel agent containing tannic acid, benzyl alcohol and xanthane gum, and (2) a second agent containing an iron salt.

12 Claims, No Drawings

HAIR DYE

TECHNICAL FIELD

The present invention relates to a hair dye for gray hair, more particularly a non-oxidative hair dye composition, which has high dyeing property and high safety.

BACKGROUND ART

Hair dye is generally classified into four types, namely, oxidative hair dye, ionic hair dye, temporary hair dye, and others. Among these hair dyes, an oxidative hair dye, which has been most widely used at present, is also referred to as a permanent hair dye, and it is mainly constituted with paraphenylenediamine or para-aminophenol that becomes an active reaction intermediate as a result of oxidation by hydrogen peroxide. The active intermediate then reacts with a dye coupler molecule in hair, and it changes to a shampoo-resistant hair dye. However, such an oxidative hair dye damages hair, may cause contact dermatitis or latent influence on total body for a long period of time, and may be suspected as mutagenicity or carcinogen. An ionic hair dye is also referred to as a semi-permanent hair dye, and it does not damage hair. However, such an ionic hair dye is problematic in term of skin coloration upon dyeing, and in that the dye is washed off from hair by performing shampooing operations four to ten times. A temporary hair dye does not damage hair, and skin coloration is overcome since washing is possible. However, such a temporary hair dye is washed off from hair by performing a single shampooing operation.

As another hair dye, there has been proposed a non-oxidative hair dye containing polyvalent phenol and an iron salt (Patent Documents 1 to 3). However, previous non-oxidative hair dyes have not been satisfactory in terms of hair dyeing property and color tone. The non-oxidative hair dyes which are currently available are only the products, base material of which is cream (emulsion).

Moreover, Patent Documents 4 and 5 disclose that the hair dye compositions which comprise a polymer containing flavan-7-ol as an essential constitution monomer may contain multivalent metal salt, xanthane gum and benzyl alcohol, but these hair dye compositions do not contain tannic acid. Also, Patent Document 6 discloses a hair dye tool where comb portion is fit to an aerosol container which contains a hair dye, and discloses that the hair dye may contain benzyl alcohol, xanthane gum, metal salt and tannic acid. However, this hair dye is not a hair dye of two-agent type. Patent Document 7 discloses a cosmetic for head hair which contains fine powders of henna plant which were pulverized into a diameter of 2 mm or less, or henna extract, wherein the cosmetic contains an antioxidizing agent, dye for hair and other various components. However, this hair dye is not a hair dye of two-agent type.

PRIOR ART DOCUMENTS

Patent Documents

Patent Document 1: JP Patent Publication (Kokai) No. 4-164017 A (1992)
Patent Document 2: JP Patent Publication (Kokai) No. 2003-246716 A
Patent Document 3: JP Patent Publication (Kokai) No. 2008-273869 A
Patent Document 4: JP Patent Publication (Kokai) No. 2001-172143 A
Patent Document 5: JP Patent Publication (Kokai) No. 2002-37720 A
Patent Document 6: JP Patent Publication (Kokai) No. 8-214936 A
Patent Document 7: JP Patent Publication (Kokai) No. 2003-48818 A

SUMMARY OF INVENTION

Object to be Solved by the Invention

A conventional hair dye, which contains a plant extract or an organic compound that reacts with an iron salt to develop color, has not been satisfactory in terms of hair dyeing property and color tone. It is an object of the present invention to provide a safe hair dye, which has a good dyeing property and is easy-to-use, and which has less uneven dyeing and has high stability of the formulation.

Means for Solving the Object

As a result of intensive studies directed towards achieving the aforementioned object, the present inventors have found that the aforementioned object can be solved by a hair dye which comprises a combination of (1) a first gel agent containing tannic acid, benzyl alcohol and xanthane gum, and (2) a second agent containing an iron salt, thereby completing the present invention.

Thus, the present invention provides a hair dye, which comprises a combination of (1) a first gel agent containing tannic acid, benzyl alcohol and xanthane gum, and (2) a second agent containing an iron salt.

Preferably, the first agent further contains a water soluble polymer having gelation property in addition to xanthane gum.

Preferably, the second agent contains xanthane gum and/or a water soluble polymer having gelation property.

Preferably, the water soluble polymer having gelation property is natural polymer or derivative thereof, cellulose derivative, or synthetic polymer or copolymer containing the same.

Preferably, the water soluble polymer having gelation property is carboxy vinyl polymer, sodium polyacrylate, acryloyldimethyl taurine ammonium/vinylpyrrolidone copolymer, polyacryloyldimethyl taurine, guar gum, locust bean gum, hydroxypropyl xanthane gum, or hydroxypropylcellulose.

Preferably, the iron salt is ferrous sulfate, ferrous chloride, ferrous acetate, ferric sulfate, ferric chloride, or ferric acetate.

Preferably, the content of the tannic acid is 0.01 to 5% by weight based on the total weight of the first agent, the content of the benzyl alcohol is 0.5 to 20% by weight based on the total weight of the first agent, the content of the xanthane gum is 0.5 to 10% by weight based on the total weight of the first agent, and the content of the iron salt is 0.5 to 10% by weight based on the total weight of the second agent.

Preferably, the first agent further contains an organic compound or plant extract which reacts with iron to develop color, in addition to tannic acid.

Preferably, the first agent further contains an antioxidizing agent.

The present invention further provides a method for dyeing hair, which comprises adding the aforementioned hair dye of the present invention to hair.

The present invention further provides a use of a combination of (1) a first gel agent containing tannic acid, benzyl alcohol and xanthane gum, and (2) a second agent containing an iron salt, for the production of a hair dye.

Effect of the Invention

The hair dye of the present invention has a good dyeing property and is easy-to-use, and has less uneven dyeing and has high stability of the formulation. The hair dye of the present invention is further excellent in safety.

EMBODIMENTS FOR CARRYING OUT THE INVENTION

Hereinafter, the embodiments for carrying out the present invention will be described in detail.

The hair dye of the present invention is a two-agent hair dye which comprises a combination of a first gel agent containing tannic acid, benzyl alcohol and xanthane gum, and a second agent containing an iron salt.

The first agent of the hair dye of the present invention contains tannic acid. The content of the tannic acid is not particularly limited, as long as the effects of the present invention are obtained, but is preferably 0.01 to 5% by weight based on the total weight of the first agent, and is more preferably 0.1 to 5% by weight based on the total weight of the first agent.

The first agent of the hair dye of the present invention contains benzyl alcohol. The content of the benzyl alcohol is not particularly limited, as long as the effects of the present invention are obtained, but is preferably 0.5 to 20% by weight based on the total weight of the first agent, and is more preferably 1 to 10% by weight based on the total weight of the first agent.

The first agent of the hair dye of the present invention contains xanthane gum. The second agent of the hair dye of the present invention may contain xanthane gum. (The second agent of the hair dye of the present invention may contain no xanthane gum.) Xanthane gum is polysaccharide which is obtained by fermentation of carbohydrate using genus *Xanthomonas*. The xanthane gum used in the present invention may include xanthane gum which is produced by using *Xanthomonas canpestris, Xanthomonas carotate, Xanthomonas incanae, Xanthomonas begonia, Xanthomonas papavericola, Xanthomonas translucens, Xanthomonas vasculorum* or *Xanthomonas hederae*, as genus *Xanthomonas*. The xanthane gum which was produced by using starch, glucose or sucrose as carbohydrate can be used. The xanthane gum which was purified by centrifugation, filtration or the like after fermentation may be used, or the xanthane gum which was purified by enzymatic treatment may be used. Further, the xanthane gum which was treated by heating or with an organic solvent may be used.

The xanthane gum may exist as an ion. The counter ion may be sodium, potassium or calcium. The viscosity of the xanthane gum may be 200 to 25000 mPa·s (type B viscometer, 6 rpm, 25° C.), and preferably 2000 to 25000 mPa·s, when an aqueous solution of xanthane gum at a concentration of 0.5% by weight is prepared. The xanthane gum may contain cellulase, and may contain no cellulase. The xanthane gum may be in powder or in granule.

The content of the xanthane gum is not particularly limited, as long as the effects of the present invention are obtained, but is preferably 0.5 to 10% by weight based on the total weight of the first agent, and is more preferably 1 to 10% by weight based on the total weight of the first agent. Also, when the second agent contains the xanthane gum, the content of the xanthane gum is not particularly limited, but is preferably 0.5 to 10% by weight based on the total weight of the second agent, and is more preferably 1 to 10% by weight based on the total weight of the second agent.

The first agent in the present invention may contains "an organic compound or plant extract which reacts with iron to develop color" other than tannic acid, in addition to tannic acid. As examples of an organic compound or plant extract which reacts with iron to develop color include, but are not limited to, gallic acid and a derivative thereof, gallnut, pyrogallol, logwood, hematein, catechol, any of oxybenzone-1 to −9, salicylic acid and a derivative thereof, phthalic acid, eugenol, isoeugenol, nicotinic-acid amide, dehydroacetic acid, pyridoxine, ellagic acid, kojic acid, maltol, ferulic acid, hinokitiol, turmeric extract, curcumin, Scutellaria root extract, onion extract, quercetin, rutin, hesperetin, hesperidin, fresh coffee bean extract, caffeic acid, chlorogenic acid, tea extract, catechin, epicatechin, lithospermi radix extract, Japanese basil extract, shisonin, grape leaf extract, grape extract, enocyanin, laccaic acid, lac, cochineal, carminic acid, elderberry, red cabbage, purple sweet potato, tamarind, kaoliang, apigeninidin, and luteolinidin. Among the above, more preferred examples include gallic acid and a derivative thereof, oxybenzone-4, salicylic acid and a derivative thereof, ferulic acid, turmeric extract, Scutellaria root extract, and quercetin. An example of the gallic acid derivative is an alkyl ester of gallic acid. An example of the gallic acid alkyl ester is a linear or branched alkyl ester containing 1 to 10, and preferably 2 to 5 carbon atoms. Specific examples of such a gallic acid alkyl ester include ethyl gallate, propyl gallate, and isoamyl gallate. Such gallic acid or a derivative thereof may be chemically synthesized according to a known method, or it may also be isolated from a plant. Moreover, it may also be prepared by further performing chemical synthesis on gallic acid or a derivative thereof isolated from a plant. Furthermore, an extract containing the gallic acid or a derivative thereof isolated from a plant may be directly used. For example, gallic acid derived from *Aralia elata* as a leguminous plant, gallic acid derived from gallnut produced from *Rhus javanica* as an anacardiaceous plant, or an extract containing the same may be used. Still further, a derivative obtained by chemically esterifying such gallic acid may also be used. Examples of the salicylic acid derivative include esters and salts of salicylic acid. Examples of the salicylic acid salt include alkali metal salts of salicylic acid. A specific example is sodium salicylate. Examples of the salicylic acid ester include a linear or branched alkyl ester and phenyl ester containing 1 to 10 carbon atoms. Specific examples of such salicylic acid ester include octyl salicylate, phenyl salicylate and methyl salicylate.

The amount of the organic compound or plant extract which reacts with iron to develop color used is not particularly limited, as long as the effects of the present invention are obtained. The amount is preferably 0.5 to 10% by weight, and more preferably 1 to 6% by weight, based on the total weight of the first agent.

The first agent of the hair dye of the present invention may further contain a water soluble polymer having gelation property in addition to the aforementioned xanthane gum. Also, the second agent of the hair dye of the present invention may contain a water soluble polymer having gelation property. The following substance may be contained as the water soluble polymer having gelation property.

(Natural Polymer Derivatives, and Derivatives Thereof)

Gum arabic, locust bean gum, gellan gum (native gellan gum), alginic acid, gum ghatti, tamarind seed gum, guar gum, carrageenan, sclerotium gum, alcasealan, karaya gum, agar, mannan, pullulan, tara gum, tragacanth gum, dextrin, pectin, inulin, hyaluronic acid, chitosan, hydroxypropyl xanthane gum, xanthan crosspolymer, hydroxypropyl guar gum, and hydroxypropyl starch phosphate.

(Cellulose Derivative)

Hydroxyethyl cellulose, hydroxypropyl cellulose, hydroxypropylmethyl cellulose, and carboxymethyl cellulose.

(Synthetic Polymer, or Copolymer Containing the Same)

Carboxy vinyl polymer, polyacrylic acid and its salt, polyacrylamide, polyvinyl alcohol, polyvinylpyrrolidone, and polyacryloyldimethyl taurine;

Acrylic acid-alkyl methacrylate copolymer, alkyl acrylate copolymer, alkyl acrylate-methacrylic acid copolymer, alkyl acrylate-alkyl methacrylate copolymer, alkyl acrylate-acrylate amide-acrylic acid copolymer, acrylic acid-vinylpyrrolidone copolymer, alkyl acrylate-vinyl acetate copolymer, acryloyldimethyl taurine ammonium-vinylpyrrolidone copolymer, acrylic acid-acryloyldimethyl taurine Na copolymer, hydroxyethyl acrylate-acryloyldimethyl taurine Na copolymer, methylvinylether-maleic acid copolymer, vinyl acetate-vinylpyrrolidone copolymer, methylvinylether-maleic anhydride copolymer.

The type of the iron salt used in the present invention is not particularly limited, as long as the effects of the present invention can be obtained. In general, ferrous sulfate, ferrous chloride, ferrous acetate, ferrous phosphate, ferrous oxalate, ferric sulfate, ferric chloride, ferric acetate, or the like can be used. Of these, ferrous sulfate or ferric chloride is preferable.

The amount of the iron salt used is not particularly limited, as long as the effects of the present invention can be obtained, and is preferably 0.5 to 10% by weight, and more preferably 1 to 6% by weight, based on the total weight of the second agent.

The first agent and/or second agent that constitute(s) the hair dye of the present invention may also comprise various types of additives, in addition to the aforementioned compounds. Examples of the additives include a surfactant, oils and fats, a solvent, organic acid, an antiseptic, an antioxidant, a pH adjuster, a wetting agent, perfume, a metallic taste masking agent, a coloring agent for products, and an ultraviolet absorber for products. As such additives, ingredients used for ordinary cosmetic products, such as a hair restorer/hair growth stimulant, an anti-dandruff agent, an antibacterial agent, a softener, a moisturizer, an active oxygen removing agent, an antioxidant, an antimicrobial agent, silicone, mineral, a protein hydrolysate, a peptide, and amino acids, may be mixed, as appropriate, within a range that does not impair the object of the present invention. The amounts of these additives used may be determined, as appropriate, within a range in which the effects of the present invention are exhibited.

Examples of the surfactant include polyoxyethylene alkyl ether, polyoxyethylene polyoxypropylene alkyl ether, glycerin fatty acid ester, polyglycerin fatty acid ester, polyethylene glycol fatty acid ester, polyoxyethylene alkyl ether phosphate and a salt thereof, alkylglucoside, N-acylamino acid salt, alkyl ether carboxylate, alkyl sulfate, polyoxyethylene alkyl ether sulfate, sulfonate, alkyl ammonium salt, and alkyl amide propyl betaine. Examples of the antioxidant include sulfite (sodium sulfite or the like), bisulfite, thiosulfate, ascorbic acid and a derivative thereof, thioglycolic acid and its analogue, cysteine and its analogue, and mercapto compound. Examples of the pH adjuster include citric acid, phosphoric acid, ammonia, ammonium bicarbonate, ammonium carbonate, potassium hydroxide, sodium hydroxide, monoethanolamine, isopropanolamine, ammonium phosphate, diammonium hydrogen phosphate (ammonium phosphate dibasic), sodium citrate, ammonium citrate, potassium phosphate, and sodium phosphate. Examples of the wetting agent include 1,3-butylene glycol, propylene glycol, glycerin, sorbitol, sodium pyrroridonecarboxylate, amino acid, and vegetable oil. Examples of the solvent include water (purified water), ethanol, isopropyl alcohol, 1,3-butylene glycol, 1,2-pentanediol, 2-methyl-2,4-pentanediol, glycerin, diglycerin, propylene glycol, and dipropylene glycol. As a protein hydrolysate, the following may be appropriately added: hydrolyzed collagen, water-soluble collagen, gelatin, hydrolyzed keratin, hydrolyzed silk, hydrolyzed conchiolin, hydrolyzed casein, hydrolyzed soybean protein, hydrolyzed wheat protein, hydrolyzed corn protein or the like.

The hair dye of the present invention is a two-agent hair dye that is composed of a first agent and a second agent, and hair dyeing is carried out by mixing the first agent with the second agent on hair. The first agent contains tannic acid, benzyl alcohol and xanthane gum, whereas the second agent contains an iron salt.

The ratio between the first agent and the second agent is preferably the first agent: the second agent=about 1:0.5 to 1:2 at a weight ratio, and particularly preferably, the first agent: the second agent=about 1:1 at a weight ratio.

The pH of the first agent is preferably pH 5 to 10, and more preferably pH 6 to 9. The pH of the second agent is preferably pH 2 to 6, and more preferably pH 3 to 5.

The dosage form of the first agent of the hair dye of the present invention is gel. Examples of the dosage form of the second agent of the hair dye of the present invention include gel, cream, liquid, emulsion, and the like, and among them, gel is preferred. Examples of the form of the container for containing the first agent or the second agent of the hair dye of the present invention include tube or aerosol type. The aerosol can be produced by filling a pressure-resistant container with the hair dye (the first agent or the second agent), compressed gas, a surfactant, a thickener, liquefied gas, etc. under an anaerobic atmosphere. The compressed gas used herein is preferably nitrogen gas, carbonic acid gas, argon gas, or the like.

Hair dyeing can be carried out by applying the above-described hair dye of the present invention to hair. As a method for applying the hair dye of the present invention to hair, the first agent may be first applied to the hair and may be then left for a predetermined period of time. Then, the second agent may be applied to the hair and may be then left for a predetermined period of time. Thereafter, the agents may be washed off. Alternatively, the first agent and the second agent may be simultaneously applied to hair, and may be then left for a predetermined period of time, followed by washing them off.

With regard to the amount of the hair dye of the present invention applied, it is preferable to apply approximately 30 to 70 g of the first agent and approximately 30 to 70 g of the second agent to hair with a length of approximately 20 cm. It is more preferable to apply approximately 40 to 60 g of the first agent and approximately 40 to 60 g of the second agent to the aforementioned hair. As an example, 50 g of the first agent and 50 g of the second agent may be applied.

Hereinafter, the present invention will be more specifically described in the following examples. However, these examples are not intended to limit the scope of the present invention.

EXAMPLES

Hair Dyeing Effects:

Hair dyeing compositions having the compositions shown in the following Tables 1 to 4 were produced by an ordinary method. The numerical value of each compound shown in the tables indicates % by weight based on the total weights of the first agent and the second agent. These compositions were evaluated in terms of hair drying property by the following methods. The results are shown in Tables 1 to 4. The amounts of sodium hydroxide and hydrochloric acid are amounts necessary for adjusting the pH to pH7.

Hair Dyeing Method:

2 g of the first agent was applied to 1 g of a goat hair bundle (part number: manufactured by Beaulax) with a length of approximately 10 cm, and it was then spread thereon uniformly. Then, it was left for a predetermined period of time. Thereafter, 2 g of the second agent was applied thereto and was then spread thereon uniformly, followed by leaving it for a predetermined period of time. Thereafter, the hair bundle was subjected to shampooing and rinsing treatments, and it was then dried with a dryer.

Method for Evaluating Hair Dyeing Property:

The color of each dyed hair bundle was measured with Chroma Meter CR200 manufactured by Minolta Corp. Hair dyeing property was evaluated based on the color difference ($\Delta E$ value) from the original white hair in accordance with the following standards.

A: 30<$\Delta E$ value (Goat hair is found fully colored by visual observation.)
B: 15≤$\Delta E$ value<30 (Goat hair is found colored by visual observation)
C: $\Delta E$ value<15 (Goat hair is found hardly colored by visual observation)

Method for Evaluating Ease of Use.

The ease of spreading at the time of application of the first agent was evaluated by 5 professional panelists in accordance with the following standards:
AA: the agent can be easily and uniformly spread without dripping
A: the agent can be uniformly spread without dripping
B: the agent cannot be uniformly spread, although dripping does not occur.
C: Dripping occurs.

Improvement of Uneven Dyeing

The dyed hair bundles were visually evaluated by 5 professional panelists in accordance with the following standards:
A: there is no uneven dyeing
B: there is uneven dyeing Stability of the Formulation The first agent which was prepared was stored in thermostat at 40° C. for 1 month. The viscosity after the storage was compared with that immediately after the preparation. The agent was visually observed. The viscosity was measured by type B viscometer at 6 rpm at 25° C.
A: the change of the viscosity is 10000 mPas or less, no separation
B: the change of the viscosity is 10000 mPas or more, and/or separation is observed
Liquid and foam was confirmed visually only.

[Table 1]

TABLE 1

| | | Dosage form | | | | | | | |
|---|---|---|---|---|---|---|---|---|---|
| | | Comparative Example 1 Liquid | Comparative Example 2 Liquid | Comparative Example 3 cream | Comparative Example 4 foam | Comparative Example 5 gel | Comparative Example 6 gel | Comparative Example 7 Gel | Comparative Example 8 Gel |
| First agent | Tannic acid | 1.0 | 1.0 | 1.0 | 1.0 | 1.0 | 1.0 | 1.0 | 1.0 |
| | Benzyl alcohol | 5.0 | 5.0 | | 2.0 | 5.0 | 5.0 | 5.0 | 5.0 |
| | Ethanol | 2.5 | 2.5 | | | 2.5 | 2.5 | 2.5 | 2.5 |
| | 1,3-Butylene glycol | 3.0 | | | | | | | |
| | Cetanol | | | 7.0 | | | | | |
| | Ceteth-20 | | | 3.0 | | | | | |
| | Glyceryl stearate | | | 2.0 | | | | | |
| | Glycerin | | | 5.0 | | | | | |
| | PEG-4 | | | | 4.0 | | | | |
| | PEG(30) | | | | 3.0 | | | | |
| | sodium laureth sulfate | | | | 1.5 | | | | |
| | Polyvinyl Alcohol | | | | 1.0 | | | | |
| | acryloyldimethyl taurine ammonium/ vinylpyrrolidone copolymer | | | | | 1.0 | | | |
| | Hydroxyethyl Cellulose | | | | | | 2.0 | | |
| | acacia gum | | | | | | | 2.0 | |
| | guar gum | | | | | | | | 1.5 |
| | sodium sulfite | 1.5 | 1.5 | 1.5 | 1.5 | 1.5 | 1.5 | 1.5 | 1.5 |
| | Potassium hydroxide | adequate dose | adequate dose | adequate dose | adequate dose | adequate dose | adequate dose | adequate dose | adequate dose |
| | hydrochloric acid | adequate dose | adequate dose | adequate dose | adequate dose | adequate dose | adequate dose | adequate dose | adequate dose |
| | Purified water | remaining amount | remaining amount | remaining amount | remaining amount | remaining amount | remaining amount | remaining amount | remaining amount |
| Second agent | Ferrous sulfate | 2.0 | | 2.0 | 2.0 | 2.0 | 2.0 | 2.0 | 2.0 |
| | Ferrous chloride | | 2.0 | | | | | | |
| | xanthane gum | 1.5 | 1.5 | 1.5 | 1.5 | 1.5 | 1.5 | 1.5 | 1.5 |
| | Purified water | remaining amount | remaining amount | remaining amount | remaining amount | remaining amount | remaining amount | remaining amount | remaining amount |

TABLE 1-continued

Dosage form

|  | Comparative Example 1 Liquid | Comparative Example 2 Liquid | Comparative Example 3 cream | Comparative Example 4 foam | Comparative Example 5 gel | Comparative Example 6 gel | Comparative Example 7 Gel | Comparative Example 8 Gel |
|---|---|---|---|---|---|---|---|---|
| Hair dyeing property | A | A | B | C | A | B | A | A |
| Ease to use | C | C | A | A | B | A | C | B |
| Uneven dyeing | A | A | B | A | A | A | B | A |
| Stability of formulation | B (separation) | B (separation) | A | A | B (separation) | A | B | B |

[Table 2]

TABLE 2

Solvent

|  |  | Comparative Example 9 | Comparative Example 10 | Comparative Example 11 | Comparative Example 12 |
|---|---|---|---|---|---|
| First agent | Tannic acid | 1.0 | 1.0 | 1.0 | 1.0 |
|  | Phenoxy ethanol |  | 5.0 |  |  |
|  | Pentyleneglycol |  |  | 5.0 |  |
|  | Ethanol | 2.5 | 2.5 |  |  |
|  | 1,3-Butylene glycol | 3.0 | 3.0 | 3.0 | 10.0 |
|  | Xanthane gum | 1.5 | 1.5 | 1.5 | 1.5 |
|  | Carboxyvinyl polymer |  |  |  | 0.25 |
|  | sodium sulfite | 1.5 | 1.5 | 1.5 | 1.5 |
|  | Potassium hydroxide | adequate dose | adequate dose | adequate dose | adequate dose |
|  | hydrochloric acid | adequate dose | adequate dose | adequate dose | adequate dose |
|  | Purified water | remaining amount | remaining amount | remaining amount | remaining amount |
| Second agent | Ferrous sulfate | 2.0 | 2.0 | 2.0 | 2.0 |
|  | Ferrous chloride |  |  |  |  |
|  | Xanthane gum | 1.5 | 1.5 | 1.5 | 1.5 |
|  | Purified water | remaining amount | remaining amount | remaining amount | remaining amount |
| Hair dyeing property |  | B | B | C | C |
| Ease to use |  | A | A | A | A |
| Uneven dyeing |  | A | A | A | A |
| Stability of formulation |  | A | A | A | A |

[Table 3]

TABLE 3

|  |  | Example 1 | Example 2 | Example 3 | Example 4 | Example 5 | Example 6 | Example 7 | Example 8 | Example 9 |
|---|---|---|---|---|---|---|---|---|---|---|
| First agent | Tannic acid | 1.0 | 1.0 | 1.0 | 1.0 | 1.0 | 0.5 | 1.0 | 1.0 | 1.0 |
|  | Hematein |  |  |  | 1.0 |  |  |  |  |  |
|  | propyl gallate |  |  |  |  | 0.2 |  |  |  |  |
|  | salicylic acid |  |  |  |  |  | 1.0 |  |  |  |
|  | Benzyl alcohol | 5.0 | 3.0 | 5.0 | 5.0 | 5.0 | 5.0 | 7.5 | 5.0 | 5.0 |
|  | Ethanol | 2.5 | 2.5 | 2.5 | 2.5 | 2.5 | 2.5 | 2.5 |  | 2.5 |
|  | 1,3-Butylene glycol | 3.0 | 3.0 | 3.0 | 3.0 | 3.0 | 3.0 | 3.0 | 3.0 | 3.0 |
|  | Xanthane gum | 2.0 | 1.5 | 1.5 | 1.5 | 1.5 | 1.5 | 1.5 | 1.5 | 1.5 |
|  | Carboxyvinyl Polymer |  |  |  |  |  |  |  |  | 0.25 |
|  | sodium sulfite | 1.5 | 1.5 | 1.5 | 1.5 | 1.5 | 1.5 | 1.5 | 1.5 | 1.5 |
|  | Potassium hydroxide | adequate dose | adequate dose | adequate dose | adequate dose | adequate dose | adequate dose | adequate dose | adequate dose | adequate dose |
|  | hydrochloric acid | adequate dose | adequate dose, | adequate close | adequate dose | adequate dose | adequate dose | adequate dose | adequate dose | adequate dose |
|  | Purified water | remaining amount | remaining amount | remaining amount | remaining amount | remaining amount | remaining amount | remaining amount | remaining amount | remaining amount |
| Second agent | Ferrous sulfate | 2.0 | 2.0 |  | 2.0 | 2.0 |  | 2.0 | 2.0 | 2.0 |
|  | Ferrous chloride |  |  | 2.0 |  |  | 2.0 |  |  |  |
|  | Xanthane gum | 1.5 | 1.5 | 1.5 | 1.5 | 1.5 | 1.5 | 1.5 | 1.5 | 1.5 |
|  | Purified water | remaining amount | remaining amount | remaining amount | remaining amount | remaining amount | remaining amount | remaining amount | remaining amount | remaining amount |
| Hair dyeing property |  | A | A | A | A | A | A | A | A | A |
| Ease to use |  | A | A | A | A | A | A | A | A | AA |
| Uneven dyeing |  | A | A | A | A | A | A | A | A | A |
| Stability of formulation |  | A | A | A | A | A | A | A | A | A |

[Table 4]

TABLE 4

|  |  | Example 10 | Example 11 | Example 12 | Example 13 | Example 14 | Example 15 | Example 16 | Example 17 |
|---|---|---|---|---|---|---|---|---|---|
| First agent | Tannic acid | 0.5 | 1.0 | 1.0 | 1.0 | 1.0 | 1.0 | 1.0 | 1.0 |
|  | Oxybenzone-4 | 1.0 |  |  |  |  |  |  |  |
|  | Salicylic acid | 1.0 |  |  |  |  |  |  |  |
|  | Benzyl alcohol | 5.0 | 3.0 | 5.0 | 5.0 | 5.0 | 5.0 | 5.5 | 5.0 |
|  | Ethanol | 2.5 | 2.5 | 2.5 | 2.5 | 2.5 | 2.5 | 2.5 | 2.5 |
|  | 1,3-Butylene glycol | 3.0 | 3.0 | 3.0 | 3.0 | 3.0 | 3.0 | 3.0 | 3.0 |
|  | Xanthane gum | 1.5 | 1.5 | 1.5 | 1.5 | 1.5 | 1.5 | 1.5 | 1.5 |
|  | Sodium polyacrylate | 0.25 | 0.25 |  |  |  |  |  |  |
|  | Acryloyldimethyl taurine ammonium/vinylpyrrolidone copolymer |  |  | 0.25 |  |  |  |  |  |
|  | Polyacryloyldimethyl taurine |  |  |  | 0.25 |  |  |  |  |
|  | Guar gum |  |  |  |  | 0.25 |  |  |  |
|  | Locust bean gum |  |  |  |  |  | 0.25 |  |  |
|  | Hydroxypropyl xanthane gum |  |  |  |  |  |  | 0.25 |  |
|  | Hydroxypropyl Cellulose |  |  |  |  |  |  |  | 0.25 |
|  | sodium sulfite | 1.5 | 1.5 | 1.5 | 1.5 | 1.5 | 1.5 | 1.5 | 1.5 |
|  | Potassium hydroxide | adequate dose | adequate dose | adequate dose | adequate dose | adequate dose | adequate dose | adequate dose | adequate dose |
|  | hydrochloric acid | adequate dose | adequate dose | adequate dose | adequate dose | adequate dose | adequate dose | adequate dose | adequate dose |
|  | Purified water | remaining amount | remaining amount | remaining amount | remaining amount | remaining amount | remaining amount | remaining amount | remaining amount |
| Second agent | Ferrous sulfate | 2.0 | 2.0 | 2.0 | 2.0 | 2.0 | 2.0 | 2.0 | 2.0 |
|  | Ferrous chloride |  |  |  |  |  |  |  |  |
|  | xanthane gum | 1.5 | 1.5 | 1.5 | 1.5 | 1.5 | 1.5 | 1.5 | 1.5 |
|  | Purified water | remaining amount | remaining amount | remaining amount | remaining amount | remaining amount | remaining amount | remaining amount | remaining amount |
| Hair dyeing property |  | A | A | A | A | A | A | A | A |
| Ease to use |  | AA | AA | AA | AA | AA | AA | AA | AA |
| Uneven dyeing |  | A | A | A | A | A | A | A | A |
| Stability of formulation |  | A | A | A | A | A | A | A | A |

The invention claimed is:

1. A hair dye, which comprises a combination of (1) a first gel agent containing tannic acid, benzyl alcohol and xanthane gum, and (2) a second agent containing an iron salt.

2. The hair dye of claim 1, wherein the first agent further contains a water soluble polymer having gelation property in addition to xanthane gum.

3. The hair dye of claim 1, wherein the second agent contains xanthane gum and/or a water soluble polymer having gelation property.

4. The hair dye of claim 2, wherein the water soluble polymer having gelation property is natural polymer or derivative thereof, cellulose derivative, or synthetic polymer or copolymer containing the same.

5. The hair dye of claim 3, wherein the water soluble polymer having gelation property is natural polymer or derivative thereof, cellulose derivative, or synthetic polymer or copolymer containing the same.

6. The hair dye of claim 4, wherein the water soluble polymer having gelation property is carboxy vinyl polymer, sodium polyacrylate, acryloyldimethyl taurine ammonium/vinylpyrrolidone copolymer, polyacryloyldimethyl taurine, guar gum, locust bean gum, hydroxypropyl xanthane gum, or hydroxypropylcellulose.

7. The hair dye of claim 5, wherein the water soluble polymer having gelation property is carboxy vinyl polymer, sodium polyacrylate, acryloyldimethyl taurine ammonium/vinylpyrrolidone copolymer, polyacryloyldimethyl taurine, guar gum, locust bean gum, hydroxypropyl xanthane gum, or hydroxypropylcellulose.

8. The hair dye of claim 1, wherein the iron salt is ferrous sulfate, ferrous chloride, ferrous acetate, ferric sulfate, ferric chloride, or ferric acetate.

9. The hair dye of claim 1, wherein the content of the tannic acid is 0.01 to 5% by weight based on the total weight of the first agent, the content of the benzyl alcohol is 0.5 to 20% by weight based on the total weight of the first agent, the content of the xanthane gum is 0.5 to 10% by weight based on the total weight of the first agent, and the content of the iron salt is 0.5 to 10% by weight based on the total weight of the second agent.

10. The hair dye of claim 1, wherein the first agent further contains an organic compound or plant extract which reacts with iron to develop color, in addition to tannic acid.

11. The hair dye of claim 1, wherein the first agent further contains an antioxidizing agent.

12. A method for dyeing hair, which comprises adding the hair dye of claim 1 to hair.

* * * * *